(12) United States Patent
Puschett

(10) Patent No.: US 8,048,868 B1
(45) Date of Patent: *Nov. 1, 2011

(54) METHOD OF PREVENTING PREECLAMPSIA

(75) Inventor: Jules B. Puschett, Temple, TX (US)

(73) Assignee: Scott & White Healthcare, Temple, TX (US)

( * ) Notice: Subject to any disclaimer, the term of this patent is extended or adjusted under 35 U.S.C. 154(b) by 192 days.

This patent is subject to a terminal disclaimer.

(21) Appl. No.: 12/501,541

(22) Filed: Jul. 13, 2009

Related U.S. Application Data

(60) Provisional application No. 61/093,465, filed on Sep. 2, 2008.

(51) Int. Cl.
*A61K 31/56* (2006.01)
*A61K 31/58* (2006.01)
*A01N 45/00* (2006.01)

(52) U.S. Cl. ............ 514/170; 514/172; 514/26; 514/25; 536/4.1

(58) Field of Classification Search .................. 514/170, 514/172, 26, 25; 536/4.1
See application file for complete search history.

(56) References Cited

U.S. PATENT DOCUMENTS

| | | |
|---|---|---|
| 2004/0171087 A1 | 9/2004 | Rech-Weichselbraun et al. |
| 2006/0134106 A1 | 6/2006 | Adair |
| 2007/0014722 A1 | 1/2007 | Puschett |
| 2007/0292968 A1 | 12/2007 | Anslyn et al. |

OTHER PUBLICATIONS

Libby et al, "Pre-eclampsia and the later development of type 2 diabetes in mothers and their children: an intergenerational study", Diabetologia (2007) 50:523-530.
Conrad, "Animal models of pre-eclampsia: do they exist?", Fetal Medicine Review 1990; 2: 67-68.
Roberts et al., "Summary of the NHLBI Working Group on Research on Hypertension During Pregnancy", Hypertension 2003; 41; 437-445, American Heart Association.
Pridjian et al., "Preeclampsia. Part 2: Experimental and Genetic Considerations", Obstetrical and Gynecological Survey, vol. 57, No. 9, pp. 619-640.
Ianosi-Irimie et al, "A Rat Model of Preeclampsia", Clinical and Experimental Hypertension, 8:605-617, 2005.
Puschett, "The role of excessive volume expansion in the pathogenesis of preeclampsia", Medical Hypotheses (2006) 67, 1125-1132.
Vu et al., "Involvement of Marinobufagenin in a Rat Model of Human Preeclampsia", Am J. Nephrol 2005;25:520-528.
Schoner, "Endogenous cardiac glycosides, a new class of steroid hormones", Eur. J. Biochem. 269, 2440-2448 (2002), FEBS 2002.
Fedorova et al., "Endogenous Na,K Pump Ligands Are Differentially Regulated During Acute NaCI Loading of Dahl Rats", Circulation. Dec. 12, 2000, pp. 3009-3014.
Uddin et al., "Marinobufagenin Inhibits Proliferation and Migration of Cytotrophoblast and CHO Cells", Placenta 29 (2008) 266-273.
Lamarca et al., "Marinobufagenin Impairs First Trimester Cytotrophoblast Differentiation", Placenta 27 (2006) 984-988.
Melamed et al., "Molecular and Kinetic Basis for the Mixed Agonist/Antagonist Activity of Estriol", Molecular Endocrinology 11: 1868-1878, 1997.
Spitz, "Progesterone receptor antagonists", Current Opinion in Investigational Drugs 2006 7 (10):882-890.
Dvela, "Diverse biological responses to different cardiotonic steroids", Pathophysiology 14 (2007 159-166.
Schoner et al., "Endogenous and Exogenous Cardiac Glycosides and their Mechanisms of Action", Am J Cardiovasc Drugs 2007 7 (3) pp. 173-187.
Feldmann et al., "Role of Endosomal Na+—K+-ATPase and cardiac steroids in the regulation of endocytosis", Am J Physical Cell Physiol 293: C885-C896, 2007.

*Primary Examiner* — Shaojia Anna Jiang
*Assistant Examiner* — Michael C Henry
(74) *Attorney, Agent, or Firm* — Eckert Seamans Cherin & Mellott, LLC; Arnold B. Silverman, Esquire

(57) ABSTRACT

A method of preventing preeclampsia including administering to a patient during an early stage of pregnancy a prophylactically-effective amount of resibufogenin. The administration of resibufogenin is periodically repeated. The method serves to prevent hypertension, proteinuria, and intrauterine growth restriction.

9 Claims, 1 Drawing Sheet

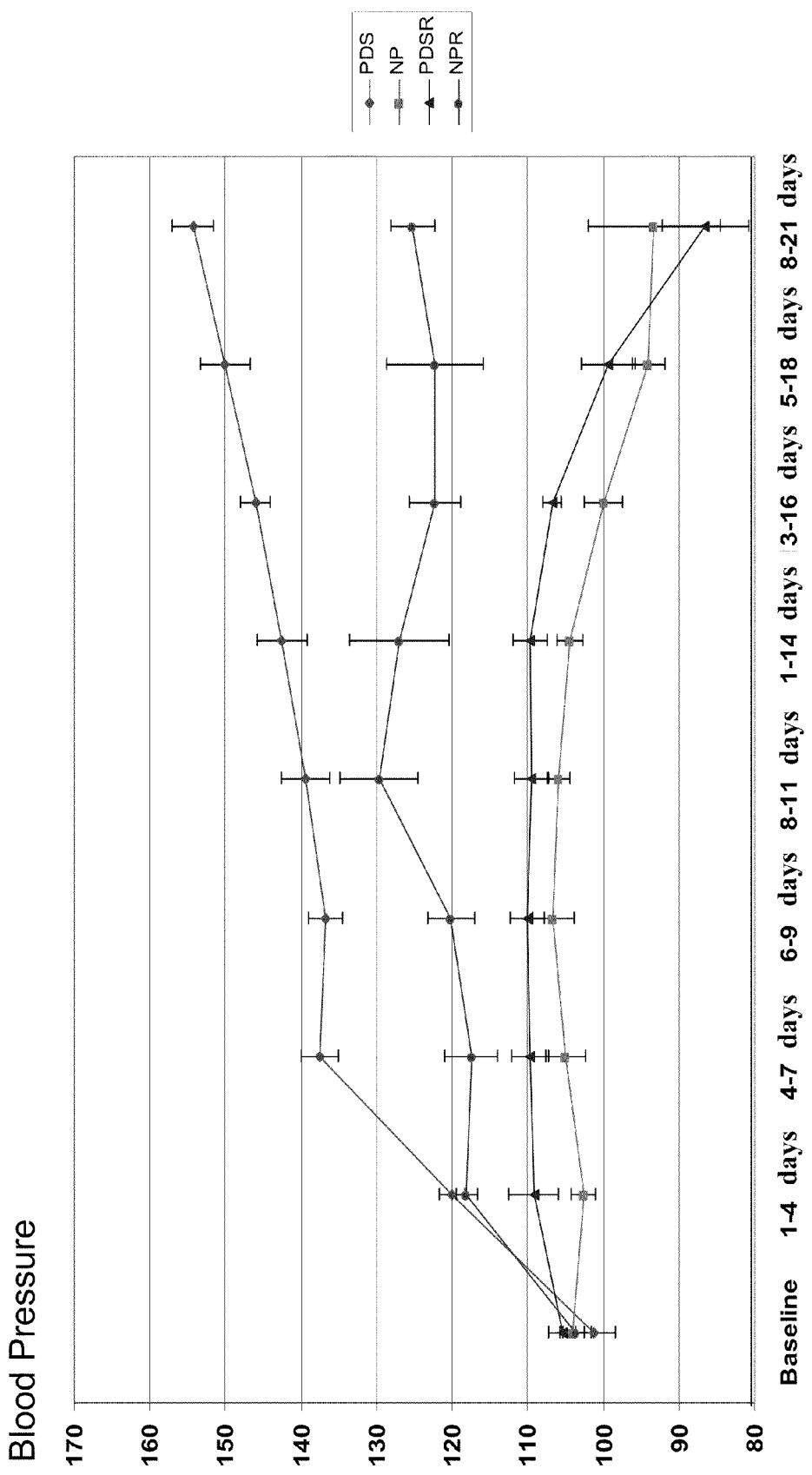
Figure ent application claims the benefit of U.S. Provi-
METHOD OF PREVENTING PREECLAMPSIA

CROSS-REFERENCE TO RELATED APPLICATION

The present application claims the benefit of U.S. Provisional Patent Application Ser. No. 61/093,465, filed Sep. 2, 2008, and entitled "Method of Preventing Preeclampsia," which is herein incorporated by reference in its entirety.

BACKGROUND OF THE INVENTION

1. Field of the Invention

The present invention relates to a method of preventing preeclampsia, and more specifically, to administering resibufogenin in early pregnancy in order to prevent preeclampsia by preventing the advent of hypertension, proteinuria, and the development of intrauterine growth restriction.

2. Description of the Prior Art

Preeclampsia remains an important problem in pregnancy. It is the second leading cause of fetal wastage and maternal and fetal morbidity in the United States and abroad Pridjian G, Puschett J B. Preeclampsia. Part 1: clinical and pathophysiologic considerations. *Obstet Gynecol Surv* 2002; 57 (9):590-8. Hazards associated with the development of the hypertension and proteinuria which characterize the disorder include progression to eclampsia and the all too frequent eventuation of intrauterine growth restriction (IUGR). Not only does the latter condition compromise fetal survival Pridjian G, Puschett J B. Preeclampsia. Part 1: clinical and pathophysiologic considerations. *Obstet Gynecol Surv* 2002; 57 (9):590-8, but may affect those children who survive with medical problems in later life Libby G, Murphy D J, McEwan N F, et al. Pre-eclampsia and the later development of type 2 diabetes in mothers and their children: an intergenerational study from the Walker cohort. *Diabetologia* 2007; 50 (3):523-30. Thus, prevention of the syndrome would represent an important advance. Indeed, as is the case with many disorders, interfering in the pathogenetic process before lasting and irreversible anatomical and pathophysiological processes have gained a foothold, may represent the only truly successful therapy.

An important problem in the development of diagnostic and therapeutic stratagems in preeclampsia has been the relative dearth of animal models Conrad K D. Animal models of preeclampsia: do they exist? *Fetal Med Rev* 1 990; 2:7-88. This is especially true of those which address the early events in its pathogenesis. Evidence has accumulated which suggests that the pathophysiologic events which result in the clinical features of preeclampsia occur long before the latter become manifest Roberts J M, Pearson G, Cutler J, Lindheimer M. Summary of the NHLBI Working Group on research on hypertension during pregnancy. *Hypertens* 2003; 41:437-445. Most likely, these baleful events occur in the first trimester Pridjian G, Puschett J B. Preeclampsia. Part II: experimental and genetic considerations. *Obstetrical and Gynecological Survey* 2002; 57:619-640.

Pregnancy represents nature's experiment in the phenomenon of volume expansion. Pregnancy results in an increase in body volume of from 40 to 50% over baseline values as gestation proceeds Scott D E. Anemia in pregnancy. *Obstet Gyn Ann* 1972; 1:219-44. We have postulated that a segment of the preeclamptic population represents a group of patients whose expansion is excessive and who have an impaired ability to excrete excess salt and water because of a defect in sodium handling by the kidneys Puschett, J B. The role of excessive volume expansion in the pathogenesis of preeclampsia. *Medical Hypotheses* 2006; 67:1125-1132.

There remains a very real and substantial need for a method of preventing preeclampsia.

SUMMARY OF THE INVENTION

The invention provides a method of preventing preeclampsia by administering, to a patient during an early stage of pregnancy, a prophylactically effective amount of resibufogenin. The administration of resibufogenin is periodically repeated. The resibufogenin may be introduced into the patient parenterally (either intravenously or intramuscularly) or orally.

The process serves to prevent hypertension, proteinuria, and intrauterine growth restriction. The patient may be a human being.

It is an object of the present invention to provide an effective method for preventing a pregnant patient from becoming preeclamptic.

It is a further object of the present invention to accomplish this prevention by administering a prophylactically-effective amount of resibufogenin with such administration being periodically repeated.

It is a further object of the present invention to provide such a method which may be employed on pregnant humans during an early stage of pregnancy.

These and other objects of the present invention will be more fully understood in the following detailed description of the invention on reference to the illustrations appended hereto.

BRIEF DESCRIPTION OF THE DRAWING

The FIGURE represents a plot of blood pressure versus time for four categories of experimental animals.

DETAILED DESCRIPTION OF THE PREFERRED EMBODIMENTS

As employed herein, the term "early stage of pregnancy" refers to a determination of the presence in a human being of an abnormally high level of marinobufagenin in urine or blood.

As employed herein, the term "patient" refers to a mammalian member of the animal kingdom including human beings.

As employed herein, the term "resibufogenin" refers to resibufogenin and/or one of its bufodienolide analogues.

In an attempt to reproduce this situation, a rat model was developed and employed in which pregnant animals are given weekly injections of the powerful mineralocorticoid desoxycorticosterone acetate (DOCA) and whose drinking water is replaced with saline Ianosi-Irimie M, Vu H V, Whitbred J M, et al. A rat model of preeclampsia. *Clin Exp Hypertens* 2005; 8:605-17. These animals develop characteristic findings of human preeclampsia including hypertension, proteinuria, excessive body weight gain and IUGR. In addition, associated with their experimental condition, they excrete increased amounts of the bufodienolide, marinobufagenin (MBG) Vu H V, Ianosi-Irimie M R, Pridjian C A, et al. Involvement of marinobufagenin in a rat model of human preeclampsia. *Am J Nephrol* 2005; 25:520-8. MBG is a cardiotonic steroid which has vasoconstrictor, natriuretic and cardiac inotropic properties Schoner W. Endogenous cardiac glycosides, a new class of steroid hormones. *Eur J Biochem* 2002; 269:2440-8. Furthermore, the increased urinary excretion of this compound precedes the development of hypertension and proteinuria Vu H V, Ianosi-Irimie M R, Pridjian C A, et al. Involvement of marinobufagenin in a rat model of human preeclampsia. *Am J Nephrol* 2005; 25:520-8. It was determined that the hypertension and proteinuria of these "preeclamptic (PDS)" rats could be corrected by the administration of another bufodienolide, resibufogenin (RBG), which is structurally similar to MBG (Vu H V, Ianosi-Irimie M, Danchuk S, et al. Resibufogenin corrects hypertension in a rat model of human preeclampsia. *Exp Biol Med* 2006; 231:215-220). Yet, in these experiments, while there was a trend toward improvement in IUGR, these findings did not achieve statistical significance. Therefore, the purpose of the study which is presented in this communication was to determine if intervention early in pregnancy would have more beneficial effects on IUGR than the administration of RBG at a time when the rodent disorder was already established.

Female Sprague-Dawley rats (200-250 g) were obtained from Charles River Laboratories (Wilmington, Mass.) and housed in the animal facility. They were allowed free access to standard rat chow and tap water. Animal care was conducted in accordance with institutional guidelines. The rats were acclimatized for 1 week prior to being studied. The animals were mated with male Sprague-Dawley rats (Charles River Laboratories, Wilmington, Mass.) weighing 275-300 g. Pregnancy was confirmed by the presence of vaginal plugs or by examination of vaginal smears. The pregnant females were then isolated from the males. Four groups of animals were studied: normal pregnant (NP) rats given tap water ad libitum (n=10), pregnant DOCA+saline (PDS) animals (n=8) injected initially with 12.5 mg of DOCA in a depot form intraperitoneally followed by 6.5 mg on a weekly basis and whose drinking water was replaced with 0.9% saline; normal pregnant rats given RBG by daily injection in a dose of 30 micrograms per kilogram body weight per day intraperitoneally beginning on day 4 of pregnancy (NPR rats, n=5); and, pregnant DOCA+saline+RBG (PDSR) animals (n=8) given daily injections of RBG in a dose of 30 micrograms per kilogram body weight per day intraperitoneally beginning on day 4 of pregnancy in addition to treatment with DOCA+saline. RBG was obtained from ChromaDex (Santa Ana, Calif.) and dissolved in dimethyl sulfoxide (DMSO). Systolic blood pressure (BP) was measured by the tail-cuff method (IITC Inc., LifeScience Instruments, model 59). For each BP value reported, 3-4 readings were performed when the BP had stabilized and the mean of these values was calculated. The measurements were obtained at the following time points: prior to pregnancy (baseline), at 1-4 days, 4-7 days, 6-9 days, 8-11 days, 11-14 days, 13-16 days, 15-18 days and 18-21 days of pregnancy. At 18-21 days of pregnancy, 24-hr urine was collected in the absence of food (this was done to eliminate contamination of the urinary protein determination by any fallen food particles). Each animal was housed separately in a metabolic cage. The rats were sacrificed at 18-21 days of pregnancy and blood was drawn. The pups were counted and inspected for malformations. The 24-hr protein excretion was measured using the pyrogallol red method (Total protein Kit, Micro Pyrogallol Red Method, Sigma).

Creatinine was measured in the blood and urine on a Nova 16 Analyzer (Waltham, Mass.) and the creatinine clearance was calculated. Hematocrit was measured using a StatSpin MP Multipurpose Centrifuge (Norwood, Mass.). Statistics were performed using analysis of variance (ANOVA) and Tukey's post-hoc test.

Blood pressure (BP) measurements were taken at nine time periods during the pregnancy and are shown in FIG. 1.

Blood pressure results for four groups of experimental animals obtained at various time periods during gestation: NP=normal pregnant rats; PDS=pregnant animals given saline in their drinking water and injected weekly with DOCA; PDSR=rats in whom resibufogenin 30 µg/kg/day) was injected at the onset of pregnancy along with DOCA and the provision of saline as drinking water; NPR=normal pregnant animals injected daily with resibufogenin 30 µg/kg/day. See text for statistical analyses.

Mean BP increased in PDS rats from 101±10 mmHg to 154±12 mmHg ($p<0.001$) at 18-21 days of pregnancy (the gestation period in the rat is 20-21 days). BP also increased in NPR rats from 104±5 mmHg to 125±6 mmHg ($p<0.05$). The final BP for PDS rats was statistically higher than the final BP for NPR rats ($p<0.001$). Mean BP decreased in NP rats from 104±6 mmHg to 93±8 mmHg ($p<0.05$). BP also decreased in PDSR rats from 105±5 mmHg to 87±6 mmHg ($p<0.001$). The final BP for PDS and NPR rats was statistically higher than the final BP for both NP and PDSR rats ($p<0.001$ for all). Final BP for NP and PDSR rats was not statistically different ($p>0.05$). The injection of RBG in a dose of 15 µg/kg/min daily did increase blood pressure but failed to prevent hypertension when given to PDS rats (data not shown).

The PDS and NPR groups showed a statistically significant increase ($p<0.05$) in protein excretion when compared with both the NP and PDSR groups. NP: 2.3±1.2 mg/24 hr; PDS: 5.4±1.0 mg/24 hr; NPR: 4.6±0.8 mg/24 hr; PDSR: 2.5±1.1 mg/24 hr. NP did not differ statistically from PDSR. NPR did not differ statistically from PDS (Table 1).

TABLE 1

|  | Number of Rats | Pups | Hematocrit | CCR | Protein Excretion |
|---|---|---|---|---|---|
| NP | 10 | 14.9 ± 1.9 | 0.34 ± 0.02 | 0.94 ± 0.34 ml/min | 2.3 ± 1.2 mg/24 hr |
| DSR 30 | 8 | 14.6 ± 1.3 | 0.33 ± 0.02 | 1.07 ± 0.29 ml/min | 2.5 ± 1.1 mg/24 hr |
| PR 30 | 5 | 11.8 ± 1.6 | 0.38 ± 0.01 | 1.20 ± 0.49 ml/min | 4.6 ± 0.8 mg/24 hr |
| DS | 8 | 11.5 ± 1.2 | 0.38 ± 0.02 | 1.22 ± 0.53 ml/min | 5.4 ± 1.0 mg/24 hr |

The creatinine clearance values for the four groups of animals were not different from each other statistically ($p>0.05$). NP: 0.94±0.34 ml/min; PDS: 1.22±0.53 ml/min; NPR: 1.20±0.49 ml/min; PDSR: 1.07±0.29 ml/min (Table 1).

The mean value for the hematocrit of 0.38±0.02 for the PDS group and 0.38±0.01 for the NPR group were statistically significantly different from those for the NP group (0.34±0.02, $p<0.02$) and for the PDSR animals (0.33±0.02, $p<0.006$). NP did not differ statistically from PDSR. NPR did not differ statistically from PDS.

The average numbers of pups for NP (14.9±1.9) and PDSR (14.6±1.3) were statistically larger than the average number of pups for NPR (11.8±1.6) and PDS rats (11.5±1.2) ($p<0.05$ in all cases). NP did not differ statistically from PDSR. NPR did not differ statistically from PDS.

MBG is a steroid hormone which circulates in the blood and is excreted in the urine. It is an inhibitor of Na+/K+ ATPase with a predilection for the alpha-1 isoform of the enzyme Federosa O V, Lakatta E G, Bagrov A Y. Endogenous Na, K pump ligands are differentially regulated during acute NaCl loading of Dahl rats. *Circulation* 2000; 102:3009-3014. In addition to its effects to cause vasoconstriction and an elevation in the blood pressure Schoner W. Endogenous cardiac glycosides, a new class of steroid hormones. *Eur J Biochem* 2002; 269:2440-8, it has been determined to cause an increase in vascular permeability in our rodent model of preeclampsia Uddin M N, McLean L B, Hunter F, et al. Marinobufagenin induces altered vascular permeability: in vivo and in vitro studies. Submitted for presentation to the *American Heart Association Annual Scientific Sessions*, New Orleans, La., Nov. 8-12, 2008. Furthermore, as mentioned earlier, its excretion in the urine of our PDS animals is increased prior to the development of hypertension and proteinuria. These observations suggest that MBG may play a role in the pathogenesis of preeclampsia and/or represent a diagnostic tool at a stage in the disease process at which the clinical manifestations have not yet become manifest. Volume expansion provides the stimulus for the secretion and elaboration of MBG Fedorova O V, Doris P A, Bagrov A Y. Endogenous marinobufagenin-like factor in acute plasma volume expansion. *Clin Exper Hypertens* 1998; 20 (5 & 6): 581-591.

In addition, blood levels of MBG have been reported to be elevated in patients with preeclampsia as well as in other forms of volume expansion-mediated hypertension Gonick H C, Ding Y, Vaziri N D, et al. Simultaneous measurement of marinobufagenin, ouabain, and hypertension-associated protein in various disease states. *Clin Exp Hypertens* 1 998; 20 (5-6):617-27.

MBG also has direct effects on cytotrophoblast (CTB) function. In vitro studies have demonstrated that the bufodienolide interferes with the properties of proliferation, migration and invasion by the CTB cells Uddin M N, Horvat D, Glaser S S, et al. Marinobufagenin inhibits proliferation and migration of cytotrophoblast and CHO cells. Placenta 2008; 29:266-273; LaMarca H L, Morris C A, Pettit G R, et al. Marinobufagenin impairs first trimester cytotrophoblast differentiation. Placenta 2006; 27 (9-10):984-988. Normal placentation involves a process in which the CTB cells invade the decidua and remodel the tributaries of the spiral arteries, converting them from high resistance, narrow channels to wide bore, high flow, low resistance vessels. In consequence, normal maternal-fetal nutrition and development are accomplished.

Our hyphthesis is there exists a group of preeclamptic patients who have a defect in the excretion of sodium Puschett, S B. The role of excessive volume expansion in the pathogenesis of preeclampsia. *Medical Hypotheses* 2006; 67:1125-1132. This abnormality does not become manifest until and unless the patient faces the burden of an increase of 40 to 50% in body volume represented by pregnancy. Accordingly, we postulate, excessive volume expansion occurs, since the patient is unable to rid herself of all of the excess salt and water. As a consequence, supraphysiologic amounts of MBG are produced, which have the following effects: they cause hypertension, proteinuria and IUGR, by virtue of the steroid's actions to cause vasoconstriction and hypertension and its interference with normal placentation.

RBG is a molecule which differs from MBG only in the absence of an hydroxyl group at the β-5 position Puschett, J B. The role of excessive volume expansion in the pathogenesis of preeclampsia. *Medical Hypotheses* 2006; 67:1125-1132. This difference in structure could confer on RBG an ability to antagonize MBG. That it also has some agonist activity is demonstrated by the fact that, given alone to normal pregnant animals, it, too, causes modest hypertension (FIG. 1). However, when administered in situations in which the secretion of MBG is elevated, it antagonizes the actions of MBG (Vu H V, Ianosi-Irimie M, Danchuk S, et al. Resibufogenin corrects hypertension in a rat model of human preeclampsia. *Exp Biol Med* 2006; 231:215-220; Danchuk S, Sukhanov S, Horvat D, et al. Effects of resibufogenin in experimental hypertension. *Am J Nephrol* 2008; 28:8-13). This interaction also obtains when MGB and RBG are administered together Danchuk S, Sukhanov S, Horvat D, et al. Effects of resibufogenin in experimental hypertension. *Am J Nephrol* 2008; 28:8-13.

The phenomenon of both agonist and antagonist activity of steroid compounds has been reported previously. Thus, Smith et al determined that 4-hydroxytamoxifen had both agonist and antagonist activity which depended upon the selective expression of co-activators and corepressors which modulate the regulation of the transcriptional activity of the estrogen receptor Smith C L, Nawaz Z, O'Malley B W. Coactivator and corepressor regulation of the agonist/antagonist activity of the mixed antiestrogen, 4-hydroxytamoxifen. *Mol Endocrinol* 1997; 11 (6):657-666. Melamed and coworkers examined the interaction between estriol and estradiol. They found that the weak estrogenic activity of estriol results from impaired estrogen receptor-estrogen response element interactions and that its antiestrogenic activity was a consequence of its ability to reduce estriol-dependent transcription Melamed M, Castano E, Notides A C, et al. Molecular and kinetic basis for the mixed agonist/antagonist activity of estriol. *Mol Endocrinol* 1997; 11 (12): 1868-1878. Similar dichotomous actions of progesterone have also been reported. Thus, as is the case with estrogen compounds, the effect of pro- and anti-progesterone molecules appears to depend upon their interaction with co-activators and/or corepressors Spitz I M. Progesterone receptor antagonists. *Curr Opin in Investig Drugs* 2006; 7 (10):882-890. The possibility that cardiac glycosides may act as functional antagonists to each other has recently been suggested by Dvela, et al Dvela M, Rosen H, Feldmann T, et al. Diverse biological responses to different cardiotonic steroids. *Pathophysiol* 2007; 14:159-166. In their studies of the effects of these compounds on endocytosis, they found that ouabain, unlike digoxin and bufalin, had no effect on endocytosed membrane traffic. However, when they added ouabain and digoxin in equimolar amounts, the digoxin effect was completely abolished Dvela M, Rosen H, Feldmann T, et al. Diverse biological responses to different cardiotonic steroids. *Pathophysiol* 2007; 14:159-166. Similar effects were obtained with bufalin. They postulated that differences in binding characteristics of the glycosides to intracellular organelles may explain these results.

Whether any of these phenomena explain the agonist/antagonist behavior of RBG is unknown. It is clear that Na+/K+ATPase acts as a signaling mechanism (signalsome) both for the cardenolides and bufodienolides Schoner W, Scheiner-Bobis G. Endogenous and exogenous cardiac glycosides and their mechanisms of action. *Am J Cardiovasc Drugs* 2007; 7 (3):173-189. There is, without intending to be limited by theory, the possibility that a separate specific receptor exists for at least some of the actions of the bufodienolides Feldmann T, Glukmann V, Medvenev E, et al. Role of endosomal Na+, K+-ATPase and cardiac steroids in the regulation of endocytosis. *Am J Physiol Cell Physiol* 2007; 293:885-896, which deserves further study.

In summary, it has been determined that RBG can prevent hypertension, proteinuria and intrauterine growth restriction in a rat model of preeclampsia. Its early administration in gestation is key to a successful outcome. These findings should have relevance for the corresponding human condition.

Whereas particular embodiments of the present invention have been described herein for purpose of illustration, it will be evident to those skilled in the art that numerous variations of the details may be made without departing from the invention as set forth in the appended claims.

What is claimed is:

1. A method of treating a pregnant patient at risk for excessive volume expansion comprising
administering to said patient an effective amount of resibufogenin at an early stage of pregnancy.
2. The method of claim 1 including
periodically repeating said administration of said resibufogenin.
3. The method of claim 2 including
introducing said resibufogenin parenterally.
4. The method of claim 2 including
repeating said method in said patient at least weekly.
5. The method of claim 2 including
repeating said method in said patient daily.
6. The method of claim 1 including
employing said method on a human being.
7. The method of claim 1 including
employing a urine specimen in determining that an early stage of pregnancy exists.
8. The method of claim 1 including
employing a blood specimen in determining that an early stage of pregnancy exists.
9. The method of claim 1 including
introducing said resibufagenin orally.

\* \* \* \* \*